United States Patent
Holoch et al.

(10) Patent No.: US 8,366,906 B2
(45) Date of Patent: Feb. 5, 2013

(54) MEASURING METHOD FOR MONITORING RESIDUAL OXYGEN IN AN EXHAUST GAS

(75) Inventors: Philip Holoch, Winterthur (CH); Thomas Gamper, Diessenhofen (CH)

(73) Assignee: Sulzer Hexis AG, Winterthur (CH)

( * ) Notice: Subject to any disclaimer, the term of this patent is extended or adjusted under 35 U.S.C. 154(b) by 942 days.

(21) Appl. No.: 12/209,118

(22) Filed: Sep. 11, 2008

(65) Prior Publication Data

US 2009/0057163 A1    Mar. 5, 2009

Related U.S. Application Data

(62) Division of application No. 10/866,404, filed on Jun. 10, 2004, now abandoned.

(30) Foreign Application Priority Data

Jul. 3, 2003 (EP) ..................................... 03405495

(51) Int. Cl.
*G01N 27/41* (2006.01)
(52) U.S. Cl. ....................... 205/784.5; 204/401; 204/425
(58) Field of Classification Search ............... 205/784.5, 205/785; 204/401, 425
See application file for complete search history.

(56) References Cited

U.S. PATENT DOCUMENTS

| | | | | |
|---|---|---|---|---|
| 4,601,809 A * | 7/1986 | Kitahara | | 204/406 |
| 4,753,203 A * | 6/1988 | Yamada | | 73/23.32 |
| 4,819,602 A * | 4/1989 | Mieno et al. | | 123/688 |
| 5,034,112 A * | 7/1991 | Murase et al. | | 204/406 |
| 5,558,752 A | 9/1996 | Wang et al. | | |
| 6,059,947 A | 5/2000 | Kato et al. | | |
| 6,471,840 B1 | 10/2002 | Gao et al. | | |
| 7,901,562 B2 * | 3/2011 | Hattori | | 205/785 |
| 2003/0116433 A1 | 6/2003 | Diehl | | |
| 2004/0089279 A1 | 5/2004 | McLaughlin et al. | | |

* cited by examiner

*Primary Examiner* — Kaj K Olsen
(74) *Attorney, Agent, or Firm* — Kilpatrick Townsend & Stockton LLP

(57) ABSTRACT

A lambda probe in which a measuring point for oxygen in a sensor is connected via a diffusion gap with a reaction chamber. The reaction chamber drives oxygen along the diffusion gap. A desired oxygen partial pressure is set in the reaction chamber. The pump current, which is proportional to the strength of the stream of oxygen driven along the diffusion gap, can be used as a measurement for the partial pressure of the residual oxygen in the exhaust gas during a normal operating phase. The lambda probe can be operated for test purposes intermittently in a high or low phase, in which the oxygen partial pressure in the reaction chamber is a minimum or maximum value. While changing between the operating phases, by comparing the pump currents with empirical values, conclusions with regard to the ability of the probe to function can be derived.

8 Claims, 1 Drawing Sheet

MEASURING METHOD FOR MONITORING RESIDUAL OXYGEN IN AN EXHAUST GAS

CROSS-REFERENCE TO RELATED APPLICATIONS

This application is a Divisional of U.S. application Ser. No. 10/866,404, filed Jun. 10, 2004, now abandoned and which claims the benefit of European Patent Application No. 03405495.7, filed Jul. 3, 2003, the disclosures of which are both incorporated herein by reference.

BACKGROUND OF THE INVENTION

The invention relates to a measuring apparatus for monitoring residual oxygen in an exhaust gas, to a method for operating the measuring apparatus, and also to a use of the method.

The measuring apparatus is a modified lambda probe (broad band lambda probe) such as is used in cars for monitoring the exhaust gases. The measuring apparatus includes a sensor and in the interior of this a "reaction chamber" in which the partial pressure of molecular oxygen is influenced via electrode reactions. This oxygen partial pressure can be changed or adjusted by means of an oxygen ion pump working electrochemically between the reaction chamber and an exhaust space. At the same time as a transport of oxygen ions in the ion pump, a transport of molecular oxygen takes place through a "diffusion gap" into the reaction chamber or out of it. The diffusion gap joins the reaction chamber with the measuring point in the exterior region of the probe at which the concentration of the residual oxygen in the exhaust gas (or its partial pressure) is determined as a desired value. The oxygen partial pressure in the reaction chamber is preset as the desired value of a regulating circuit. The actual value of this regulating circuit is determined electrochemically by means of a Nernst cell with respect to a reference value which is given by the oxygen partial pressure of the atmosphere. An electrical "pump current" with which an oxygen outflow or inflow is brought about in the oxygen ion pump is the set value of the regulating current. A steady state sets in in which the diffusion current of the molecular oxygen through the diffusion gap and the oxygen ion current in the ion pump are the same size. The difference between the oxygen partial pressure in the exhaust gas and that of the reaction chamber results in a pump current which can not only be positive but also negative.

The Nernst cell and the oxygen ion pump respectively include an oxygen ion conducting solid electrolyte layer and electrode layers applied on this layer by means of which redox processes result with molecular oxygen, with oxygen ions of the solid electrolyte layer and with electrons. The solid electrolytes are only conductive for the oxygen ions at a high temperature.

The electrons in the oxygen ion pump are introduced or removed via an electrical circuit at the electrodes; in this arrangement they form the pump current. In the steady state condition the strength of the pump current can be used as a measure for the concentration of the residual oxygen in the exhaust gas which is to be measured. The voltage determined using the Nernst cell is compared in an electronic measuring apparatus with a reference voltage which corresponds to the desired value of the partial pressure in the reaction chamber. The strength of the pump current is regulated to adapt the actual value to the desired value.

When using a fuel, in particular a gaseous or gasified fuel for room heating purposes, an energy saving procedure consists of producing electrical energy by means of fuel cells in addition to the production of thermal energy. In this or other electrochemical reactions such as in combustion of the fuel, precautionary measures are prescribed. A measure of this kind can be the use of a measuring apparatus for monitoring the residual oxygen in the exhaust gases which arise during the production of energy in order to avoid a less than stoichiometric combustion and a formation of explosive or toxic gases. An example of a system with a Lambda probe is described in EP-A-0 818 840 (FIG. 7). During the monitoring of the residual oxygen a reliable "intrinsically safe" functional reliability of the probe used for the measurement is of great importance. At any time during the operation of the fuel cell unit, one has to know whether the measuring apparatus is carrying out the monitoring correctly.

Diverse defects can arise when using a Lambda probe: cracks for example in the solid electrolyte layers of the ion pump and the Nernst cell; blocking of the diffusion gap with soot; an increase in the heat resistance; and a drift of the internal resistance of the Nernst cell as a consequence of aging.

SUMMARY OF THE INVENTION

An object of the present invention is to produce a measuring apparatus for monitoring the residual oxygen in an exhaust gas, the condition of which is monitored by a supplementary procedure in order to facilitate a timely intervention using remedial measures if defects in the measuring apparatus occur.

A Lambda probe is used with the measuring apparatus for monitoring residual oxygen in an exhaust gas in which a measuring point for oxygen at a sensor is connected with a reaction chamber via a diffusion gap. In the operation of the probe the reaction chamber drives a stream of oxygen $I_{O2}$ along the diffusion gap by means of a controllably adjustable oxygen partial pressure $p_i$. An oxygen partial pressure $p_i$ pre-determined as a desired value is set up in the reaction chamber by means of an electrochemical oxygen ion pump driven by an electrical pump current $I_p$. In this arrangement the pump current, the strength of which is proportional to the strength of the oxygen current driven along the diffusion gap, can be used as a measured variable for the partial pressure $p_m$ of the residual oxygen in the exhaust gas or its concentration. During a normal operating phase, phase N, the residual oxygen can be monitored. For test purposes the Lambda probe can be operated temporarily, in particularly intermittently in a phase H or a phase L. In these operating phases H and L the oxygen partial pressure $p_i$ in the reaction chamber assumes a largely minimum value or a largely maximum value. By means of changing between the named operating phases, by registering the pump current $I_p$ and by comparing the registered pump currents $I_p$ with empirical values, conclusions regarding the ability of the probe to function can be derived, so that if needed, in the case of a faulty or lacking ability to function, measures can be introduced to remedy the deficiencies or to exchange the sensor or for an electrochemical conversion.

BRIEF DESCRIPTION OF THE DRAWINGS

The invention will be explained on the basis of the drawings which show.

DESCRIPTION OF THE PREFERRED EMBODIMENTS

Figure 1:
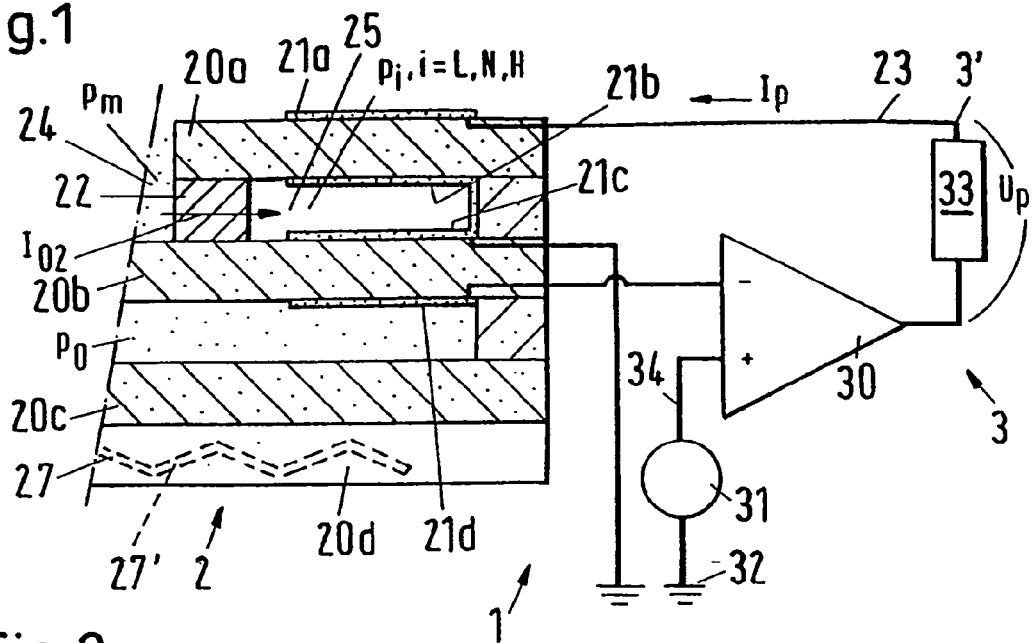
FIG. 1 is a section through a part of a Lambda probe.

A Lambda probe 1, as schematically illustrated in FIG. 1, includes a sensor 2 and an electronic part 3. These two components 2 and 3 form a part of the measuring apparatus in accordance with the invention with which the residual oxygen in an exhaust gas can be measured. A reaction chamber 25 is located in the interior of the sensor 2 in which the partial pressure $p_i$ can be influenced by molecular oxygen by means of electrochemical reactions which take place on an electrode. This oxygen partial pressure $p_i$ can be changed by means of an electrochemical oxygen ion pump working between the reaction chamber 25 and the exhaust gas. At the same time as the transport of the ions, a transport of molecular oxygen takes place through a diffusion gap 22 into the reaction chamber 25 or out of it. The diffusion gap 22, which can consist of a porous material containing fine and communicating pores, connects the reaction chamber 25 with a measuring point 24 at which the partial pressure $p_m$ of the residual oxygen in the exhaust gas is determined. The stream of the oxygen diffused by the diffusion gap 22 is termed $I_{O2}$.

The oxygen partial pressure $p_m$ is determined electrochemically by means of a Nernst cell with reference to a reference value which is given by means of the partial pressure $p_0$ of the atmospheric oxygen existing in the environment. The relative proportion of the oxygen in the atmosphere amounts to 21% by volume.

The oxygen pump and the Nernst cell respectively include a negative ion conducting solid electrolyte layer 20a, or 20b. The solid electrolytes are only conductive for the oxygen ions at a high temperature. A temperature of preferably 750° C. is produced by means of a heater 27 integrated in the sensor 2. An electric heating element 27' made of platinum is embedded in an outer base plate 20d, which is thermally conductively adjacent to an inner base plate 20c.

Electrodes 21a, 21b and 21c and 21d are applied to the relatively thick solid electrolyte layers 20a and 20b as thin layers. The electrode 21b of the oxygen ion pump is electrically conductingly connected to the electrode 21c of the Nernst cell. These two electrodes 21b and 21c cover a large part of the inner surface of the reaction chamber 25. Redox processes take place on the electrodes between molecular oxygen, oxygen ions of the solid electrolyte layers and electrons. In the case of the oxygen ion pump, the electrons are respectively supplied by and led away by an electrical circuit 3' at the electrodes 21a and 21b; in this arrangement they form a pump current $I_p$. If a steady state is present for the oxygen ion pump, the strength of the pump current $I_p$ can be used as a measurement for the concentration of the residual oxygen to be measured in the exhaust gas.

The oxygen stream $I_{O2}$ flowing through the diffusion gap 22 is driven due to the difference of the partial pressures $p_m$ and $p_i$. In a stationary condition, $I_{o2}$ is proportional to the pump current $I_p$. Using the pump current $I_p$, the oxygen partial pressure $p_i$ in the reaction chamber is adjusted to a desired value using the Nernst cell. In this arrangement the voltage determined using the Nernst cell which corresponds to the actual value of $p_i$ is compared in the electronic part 3 with a reference voltage which corresponds to the desired value of $p_i$. The reference voltage is produced in a component 31 which is arranged on a connection 34 between ground 32 and the input of an operational amplifier. At the output of the amplifier 30 the pump current $I_p$ flows through a line 23 to the electrode 21a of the oxygen ion pump. The line 23 contains an ohmic resistance 33 at which the pump current $I_p$ can be measured as voltage $U_p$. The strength of the pump current $I_p$ is regulated to adapt the actual value to the desired value of $p_i$.

The known Lambda probe 1 is usually operated using a fixed reference voltage (450 mV for example) of the component 31 so that a constant oxygen partial pressure $p_i$ sets in in the reaction chamber 25. In the method in accordance with the invention the reference voltage is dynamically driven in a large range by respectively changing from one reference voltage to the next one after short phases (time intervals). Thus new values are continually set for the oxygen partial pressure $p_i$ in the reaction chamber. During a normal operating phase, termed phase N in the following, the partial pressure $p_m$ of the residual oxygen is measured. For test purposes the Lambda probe 1 is operated from time to time in a phase H or in a phase L. In these phases H and L, $p_i$ assumes a largely minimum value ($p_H \approx p_m$) or a largely maximum value ($p_L \approx p_0$) in the reaction chamber 25.

A dynamic signal results correspondingly for the pump current $I_p$. It is important in the method according to the invention that the reference voltage given by the component 31 is varied up to the limits possible electrochemically. In the corresponding boundary ranges a largely maximum voltage of approximately 1 V (=no-load voltage of the Nernst cell) results for the Nernst cell or a largely minimum voltage of approximately 0 V. In correspondence with the value of the respective reference voltage, the phases are termed phase H, phase N and phase L (based on "high", "normal" and "low"). The reference voltages typically amount to 900 mV (for H), 450 mV (for N) and 20 mV (for L).

With reference to the limiting voltages of the Nernst cell, the oxygen partial pressure $p_i$ in the reaction chamber 25 assumes values which differ by several powers of ten. Due to the large differences, an amplification results for the pump current $I_p$, which, when compared with the usual amplification of pump currents, is very much greater. Due to this amplification, defects which have an influence of the transport of the molecular oxygen into the reaction chamber 25 are easily recognizable.

If one knows the ratios between the pump currents $I_p$ at different reference voltages of a new, intact probe 1 and enters these values electronically into a table, then one can easily recognize defect probes in an electronic logic circuit. In particular one can recognize the formation of a defect at an early stage—prior to the actual measuring signal failure of the normal measurement (phase N, 450 mV reference voltage).

Temperature swings have an influence on the permeability of the diffusion gap 22 and on the ion mobility of the oxygen pump and thus on the probe signal. For this reason, the power of the electrical heating 27, with which the sensor 2 is kept at the pre-given temperature, is regulated. To this end the internal resistance of the Nernst cell is not used, as is common, since this is subjected to severe aging. Instead a heating current is briefly interrupted in phases and during this interruption the resistance of the heating element 27' is measured. This measured value is a measurement for the temperature of the sensor 2. In the new state the temperature control can be calibrated with regard to the inner resistance because the value of this inner resistance is known for the new state. For the calibration a regulation is effected once to the inner resistance of the Nernst cell. As soon as this corresponds with a desired value, the actual value of the resistance of the heating element is taken/recorded. This value can subsequently be taken as a desired value for the heating power control during the whole life of the sensor 2.

When registering a change in the heater resistance a corresponding correction in the strength of the thermal flow is carried out by means of a control circuit, in order to maintain a pre-given operating temperature (750° C.) of the sensor.

During the phase N the residual oxygen in the exhaust gas is monitored. From time to time, in particular intermittently, the Lambda probe is operated in the phase H or in the phase L, with the oxygen partial pressure in the reaction chamber 25 assuming largely extreme values in these operating phases. Conclusions regarding the ability of the probe to function can be derived by means of changing between the named operating phases, by registering the pump current $I_p$ and by comparison of the pump current with values known from experience. Thus if necessary, in the case of a lacking or faulty ability to function, measures can be introduced to remedy the deficiencies or to exchange the sensor 2.

Figure 2:
FIG. 2 is a graphic illustration of the pump current in the dynamic operation of the measuring apparatus in accordance with the invention for a lean exhaust gas ($\lambda \gg 1$)

FIG. 2 shows the dynamic signal of a pump current $I_p$, if a lean exhaust gas ($\lambda \gg 1$) forms an oxygen source at the measuring point 24 which has a high oxygen partial pressure $p_m$ of about $10^4$ Pa. The reference voltage of the component 31 which determines the desired value in relation to $p_i$ is continually varied step-by-step with the progress of time from low to medium (normal), from medium to high and from high to low and periodically in this manner so that a periodic sequence of the phases L, N and H sets in. For the phase L, $p_1$ is around $10^2$ Pa ($=p_L$), for N around $10^{-7}$ Pa ($=p_N$) and for H around $10^{-15}$ Pa ($=p_H$). The reference voltage of the component 31 is left unchanged at each step during a time interval, at least until a steady state has set in. The settling requires three seconds for example. The operating phases N, L and/or H can last for different lengths of time.

For the pump current $I_p$, which is proportional to the difference between $p_m$ and $p_i$, relatively large values result for all three operating phases L, N and H. The pump current $I_p$ is only disrupted for a short while during the transition from the phase H to the phase L and even shows a change in the flow direction. At this transition the oxygen partial pressure $p_i$ in the reaction chamber has to be increased considerably, from practically zero to around $10^2$ Pa. This increase mainly results from an inflow of molecular oxygen from the exhaust gas of the measuring point 24. The phases N and H cannot be distinguished from each other on the basis of the graph in the diagram of FIG. 2.

Figure 3:
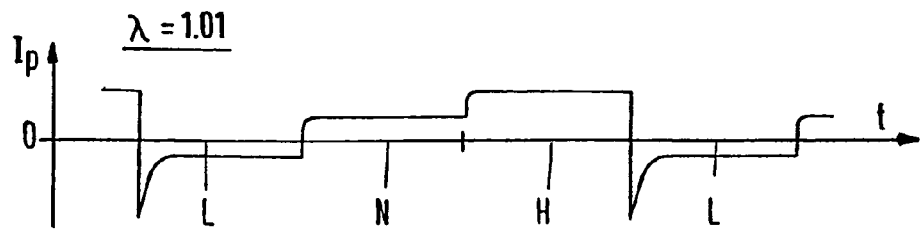
FIGS. 3, 4 are corresponding illustrations for rich exhaust gases the λ of which amounts to approximately 1 (λ=1.01 and λ=0.95).
Figure 4:
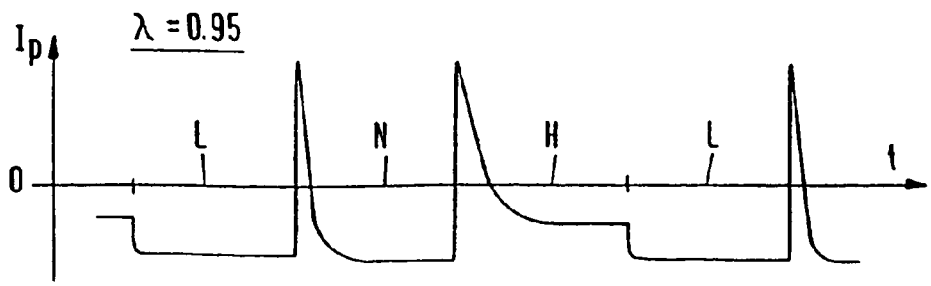

FIG. 3 shows the dynamic signal of a pump current $I_p$ if a rich exhaust gas forms an oxygen source with $\lambda=1.01$ which has a low oxygen partial pressure $p_m$ of around 10 Pa. The measuring point 24 even forms a negative oxygen source in the phase L, in other words, an oxygen sink. FIG. 4 shows the dynamic signal of a pump current $I_p$, if a rich exhaust gas with $\lambda=0.95$ forms an oxygen sink with a very small oxygen partial pressure $p_m$ of around $10^{-15}$ Pa. In the steady states the currents flow in the opposite direction than with the lean exhaust gas (FIG. 2). The phases N and L can only be distinguished from one another on the basis of the graph at the profile directly after the transitions from L to N and from H to L.

The method in accordance with the invention can be used in an apparatus in which exhaust gases have to be monitored during combustion or in an electrochemical reaction. The apparatus can be a vehicle or a heating apparatus. The method in accordance with the invention is particularly suitable in a fuel cell system with which not only thermal energy but also electrical energy can be produced simultaneously from one fuel.

The invention claimed is:

1. A method for monitoring residual oxygen in an exhaust gas using a lambda probe in which a measuring point for oxygen at a sensor is connected with a reaction chamber via a diffusion gap, which during operation of the probe drives a stream of oxygen $I_{O2}$ along the diffusion gap by means of a controllably adjustable oxygen partial pressure $p_i$, with a predetermined oxygen partial pressure $p_i$ being set in the reaction chamber as a desired value by an electrochemical oxygen ion pump driven by an electrical pump current $I_p$, and thus the pump current, the strength of which is proportional to the strength of the oxygen stream driven along the diffusion gap, can be used as a measurement parameter for the partial pressure $p_m$ of the residual oxygen in the exhaust gas, comprising:

monitoring the residual oxygen during a normal operating phase (N) to obtain a normal operating phase pump current, operating the lambda probe intermittently for test purposes in two phases (H, L) in which operating phases the oxygen partial pressure $p_i$ in the reaction chamber adopts a minimum value and a maximum value respectively, thereby obtaining a high and a low operating phase pump current, respectively, and changing between the named operating phases, by registering the respective pump currents $I_p$, comparing the pump currents $I_p$ with empirical values, and deriving conclusions with regard to the ability of the probe to function from this comparison so that in the case of a lacking or faulty ability to function, measures can be introduced to exchange the sensor.

2. A method in accordance with claim 1, wherein the oxygen partial pressure $p_i$ in the reaction chamber is determined as an actual value electrochemically by means of a Nernst cell, wherein the desired value is set by comparison with a desired value determining reference voltage and by a regulation of the pump current $I_p$, and wherein a high reference voltage, a medium reference voltage and a low reference voltage are respectively preset for the selection of the phases (H, N and L).

3. A method for operating a measuring apparatus in accordance with claim 1, wherein, except in the normal operating phase (N), the measuring apparatus is intermittently operated in the phase (L) and/or alternatingly in the phase (H) by changing the reference voltage determining the desired value in steps between medium, high and/or low.

4. A method in accordance with claim 3, wherein the reference voltage determining the desired value is continuously varied stepwise from low to medium to high and periodically in this manner.

5. A method in accordance with claim 3, wherein the reference voltage is left unchanged at every step during a time interval, at least until a settled state has been set wherein the operating phases (N, L and/or H) can last for differing lengths of time.

6. A method in accordance with claim 1, wherein an ohmic resistance heater for a solid electrolyte which is integrated in the sensor is checked periodically with the heater current switched off during the checking of the heater resistance.

7. A method in accordance with claim 6, further comprising correcting the strength of the heater current when registering a change of the heater resistance by means of a regulating current in order to maintain a pre-determined operating temperature of the sensor.

8. A method in accordance with claim 1, wherein exhaust gases of a combustion process or of an electrochemical conversion in an apparatus are monitored, with the apparatus being a vehicle, a heating device or a fuel cell system with which not only thermal energy but also electrical energy can be produced simultaneously from a fuel.

* * * * *